United States Patent [19]

Koch et al.

[11] Patent Number: 4,818,106
[45] Date of Patent: Apr. 4, 1989

[54] SPECTRAL ANALYSIS DEVICE ON A CONVERTER

[75] Inventors: Karl-Heinz Koch; Fritz Meininghaus; Hermann J. Kopineck; Wilhelm Tappe, all of Dortmund, Fed. Rep. of Germany

[73] Assignee: Hoesch Stahl Aktiengesellschaft, Dortmund, Fed. Rep. of Germany

[21] Appl. No.: 47,021

[22] Filed: May 5, 1987

[30] Foreign Application Priority Data

May 27, 1986 [DE] Fed. Rep. of Germany ....... 3617869

[51] Int. Cl.$^4$ ...................... G01J 3/443; G01N 21/63
[52] U.S. Cl. .................................................... 356/318
[58] Field of Search ................................ 356/318, 317

[56] References Cited

FOREIGN PATENT DOCUMENTS 2138540 2/1973 Fed. Rep. of Germany ...... 356/318

Primary Examiner—F. L. Evans
Attorney, Agent, or Firm—Thomas S. Baker, Jr.

[57] ABSTRACT

A spectral analysis device for determining the additions to the steel and an apparatus for generating laser beams are connected via adjustable and switchable couplable optical waveguides to the agitating gas nozzles disposed in the bottom of a converter, the radiation passing through the agitating gas nozzles being converted via metallized agitating gas nozzles and photoamplifiers to measurable intensities.

12 Claims, 1 Drawing Sheet

SPECTRAL ANALYSIS DEVICE ON A CONVERTER

The invention relates to a spectral analysis device on a converter or other container or furnace filled with liquid metal, in particular iron or steel, in which an opening extending from the outside through a wall of the container up to the molten content and filled with inert gas is optically connected for radiation emanates from the melt to the unit for spectral analysis disposed on the outer wall of the converter and through said opening in addition a laser beam is radiantly directed into the converter onto the melt.

Such a spectral analysis device is known from German patent application No. 2,138,540. This device has the disadvantage that the opening must have a relatively large diameter to ensure that an adequately large amount of radiation penetrates through the opening because the distance to the means for the spectral analysis is relatively great because of the approximately 1 m thick lining of the converter with refractory material.

This large opening is attacked at its edge by the molten steel after a short operating time to such an extent that its diameter becomes increasingly larger and as a result the lining of the converter develops a fault and becomes unusable. It has been found that such erosions do not occur with openings of very small diameter and with high exit flow speeds of the cooling inert gas. Such an opening with an extremely small diameter has compared with the opening described in German patent application No. 2,138,540 the disadvantage that only very little of the radiation to be analyzed passes through said opening. The radiation intensity is also greatly reduced due to the fact that the inert gas emerging with high speed immediately dilutes and carries away the vapour layer formed by the laser beam and stimulated to irradiate.

The problem underlying the invention is therefore to form the entire spectral analysis apparatus in such a manner that the opening is not partially clogged by solidifying melt cooled by the inert gas and also not eroded by the melt and that in spite of the length and small diameter of the opening a very accurate and evaluatable measurement is obtained and the devices can be installed simply with small constructional expenditure as reliable systems.

Due to the small cross-section of the opening and the flushing gas emerging at over 5 bar pressure, preferably inert gases Ar or $N_2$ gas, the opening is adequately cooled to prevent its edges burning away or being greatly chemically attacked whilst on the other hand the gas ensures that no cooled steel can settle because the gas tears away at high speed from the opening even the most minute particles.

The lining of the converter or other container is eroded in the course of the operating period by the melt and becomes increasingly thinner. This makes it necessary to adjust the focal point of the emerging laser beam. The simplest possibility of adjustment is for the optical waveguide with its lens disposed at the end in the opening to be pulled back at regular intervals. This also has the advantage that the optical waveguide does not come so close to the melt and thus to the high temperature region that it is damaged by the action of heat thereof and becomes opaque. This withdrawal or pulling back can also take place automatically.

To prevent the laser beam radiating against the wall of the opening in the event of small adjustment inaccuracies it is advantageous for the optical waveguide conducting said beam into the opening to lie exactly in the longitudinal axis of said opening and the optical waveguides conducting the radiation to be analyzed to be arranged round said optical waveguide.

The rapidly occurring blast operations result in a converter in that there are at least local differences in the composition of the steel. To maintain an exact as possible average value for the composition of the steel the latter must be analyzed at several points of the converter. It is therefore advantageous to install an analysis device at each of several openings of the agitating gas nozzles provided in anycase at the bottom of the converter. The high apparatus expenditure is simplified in that each opening is connected via an optical waveguide to a common analyzing unit or a common generating means for laser beams.

The light to be analyzed has an extremely small intensity because the high speed of the emerging inert gas immediately blows away the vapour stimulated to illuminate by the laser beam and consequently only an extremely thin vapour layer illuminates.

The light beam not coinciding exactly with the direction of the longitudinal axis of the opening are also conducted through the long thin opening to the analyzing unit if the inner walls of the opening are metallized for example with a thin aluminum layer. This step substantially increases the amount of light passing through the opening. The adjusting means at the optical waveguides ensures apart from the correct focal point adjustment of the laser beam also that the optical waveguides can be located as far as possible in the direction towards the melt, thus also increasing the incident amount of light. The optical waveguides are retracted by the adjusting means always to such an extent that their temperature cannot rise to an amount which would damage them. The extremely small light intensity to be analyzed is not easy to analyze reliably and accurately. On the contrary, it requires special arrangements.

Thus, it is for example expedient to form the rear end of the analysis optical waveguide such that it forms the entrance gap of a spectral unit disposed at or in the bottom of the converter to obtain the shortest possible optical wave paths. It has been found particularly advantageous to employ a monochromator effective in the associated UV range with which light amplifier devices associated with the individual lines are associated, e.g. multichannel plates. Since the element amounts present of interest may be very small the associated radiation intensities are also very small. It may therefore be expedient to carry out within the optical waveguide system an electrooptical amplification of the spectral useful signal with means known per se. Since the analytical supervision of a steel melt during the production in an LD converter requires the analysis of relatively few elements (e.g. C, S, T, Si), since many of the characteristic lines lie in the UV range, it is particularly advantageous to carry out the spectral measurement of these lines as close as possible to the beam entry point. It is furthermore advantageous to dispose in the course of the optical waveguide system conducting the spectral light received one or more narrow-band analyzing components, such as interference filters with associated light measurement systems, preferably photodetectors.

An example of the invention will be explained in detail with the aid of FIGS. 1 and 2.

Figure 1:
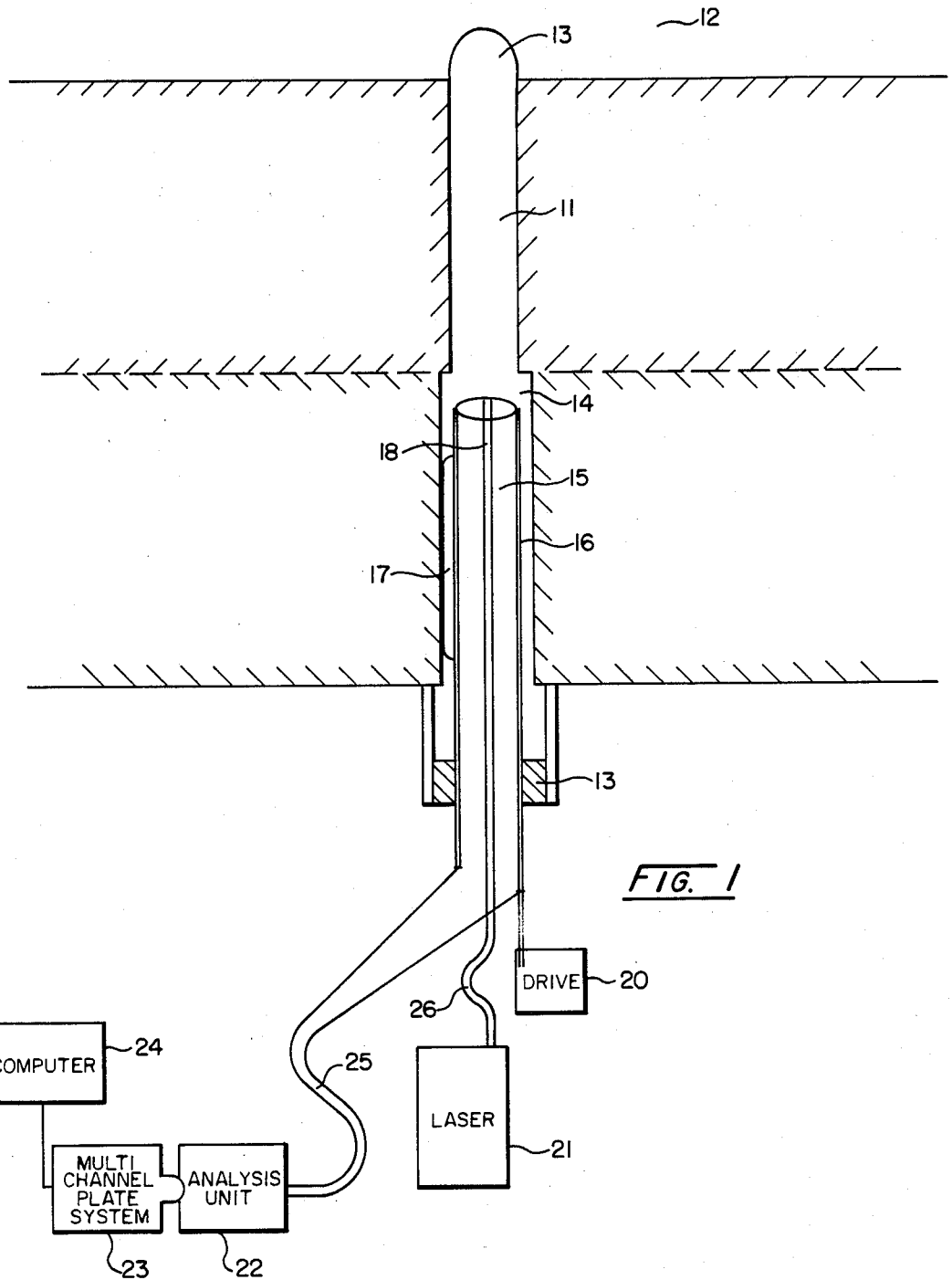
FIG. 1 is a schematic view of the spectral analysis device of the present invention in a converter.

FIG. 1 shows part of the bottom of a converter in which the opening 11 is disposed. Opening 11 has a cross-sectional area of less than one square centimeter. In the upper space 12 of the melt by the emerging inert gas a substantially hemispherical free space 13 is formed. Preferably, the inert gas flows at a rate of at least 10 grams per minute with respect to a cross-sectional area of one square millimeter. The opening 11 is widened in its lower portion 14. The opening 11 consists of a steel tube which is sealingly embedded into the refractory material of the converter. In the lower portion 14 of the opening the optical waveguide 15 is installed. It is surrounded by a thin-walled internally metallized tube 16. Attached to the tube 16 are 3 to 4 supporting ribs 17 which are guided at the wall of the lower portion 14 of the opening. In the centre of the optical waveguide 15 an optical waveguide 18 is located for entry of the laser beam. The interior of the opening 11 and 14 is sealed by a seal 19 with respect to the outer atmosphere. The tube 16 with the optical waveguides 15, 18 is adapted to be retracted out of the opening 11 and 14 stepwise or continuously by the drive 20 for adapting the focal point of the laser to the diminishing lining width in operation. The end of the laser beam optical waveguide adjacent the melted metal is positioned centrally of the longitudinal axis of the opening and occupies less than 20% of the cross-sectional area of the opening. An annular array of optical fibers surrounds the optical waveguide (18). The optical waveguide or fibre 18 is led to the generating means 21 and the optical waveguide or fibre 15 to the analysis unit 22. Additionally the exit point of the optical waveguide for the radiation is formed as a rectangular aperture and is installed in the inlet aperture of the analysis unit (22). Attached to the analysis unit 22 is the multichannel plate system 23 whose output supplies currents corresponding to the light intensities of the spectral lines to the computer 24 which calculates from said currents with the aid of a suitable program the proportions of the admixtures to the steel. In another embodiment the optical waveguides are interrupted at the points 25 and 26. At the point 26 the light of the laser is conducted via a movable mirror acting like switch-points to optical waveguides which lead to other openings also employed for measuring purposes. The radiation coming from said openings can be reflected by a likewise movable mirror installed at 25 into the optical waveguide leading to the analysis unit 22.

Figure 2:
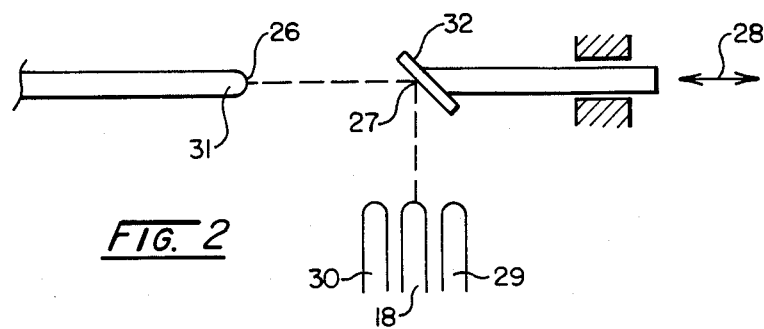
FIG. 2 is a schematic view of a portion of a second embodiment of the present invention.

The principle of such a movable mirror is illustrated in FIG. 2.

The laser beam conducted for example from the generating unit 21 of the laser beam through the optical waveguide leaves the latter through the lens 31 at the point 26 and impinges on the mirror 32 at the point 27 and is reflected to the optical waveguide 18. On displacement of the mirror 32 in the direction 28 the reflected beam is directed to he optical waveguides 29 or 30. Said optical waveguides 29 or 30 lead to other openings disposed in the bottom of the converter. The radiation arriving from said openings through the optical waveguides can be reflected in the same manner to the optical waveguide leading to the analysis unit. The mirror 32 must however then be surrounded by a housing which to avoid absorption losses is evacuated or filled with an inert gas.

The analysis unit functions normally in conventional manner with a prism or grating. It has been found advantageous to form the exit end of the optical waveguide as slit inlet aperture of the analysis unit. It is however also possible to divide the total radiation into several branches and provide each branch with a narrow-band filter which only allows the desired spectral light to pass. The latter is in turn electrooptically amplified and further processed as described.

We claim:

1. A spectral analysis device for use on a container filled with molten liquid metal, in particular iron or steel, having an opening extending from outside the container through a wall of the container up to the molten metal content and filled with inert gas, a unit for spectral analysis disposed on an outer wall surface of the container and optically connected to receive radiation emanating from said molten metal, a laser beam generating means for generating a laser beam said laser beam being radiantly directed through said opening into the container and onto the melt, whereon parts of the melt are vaporized and stimulated to emit an element-specific natural radiation, said generating means for the laser beam and said spectral analysis unit being each connected to the opening by an optical waveguide and a computer connected to the spectral analysis device, characterized in that the opening in said wall into the melt (12) has a cross-sectional area less than 1 square cm and the exit speed of the gas has a minimum velocity such that at least 10 grams per minute of gas emerge with respect to a cross-sectional area of 1 square mm and adjustment means connected to the optical waveguide wherein the focal point of the laser beam may be set at different distances from the outer wall of the container.

2. A spectral analysis device according to claim 1, characterized in that the optical waveguide for the laser beam (18) is positioned in a longitudinal direction in the outer portion (14) of the opening and including an adjusting means connected to said laser beam waveguide for adjusting the position of said laser beam waveguide in said opening.

3. A spectral analysis device according to claim 1, characterized wherein the optical waveguide (15) is connected to an adjustment means to adjust the position of said optical waveguide (15) in a longitudinal direction.

4. A spectral analysis device according to claim 1, characterized in that the end of the laser beam optical waveguide (18) directed toward the molten metal lies centrally in the longitudinal axis of the opening (14) and fills less than 20% of the cross-sectional area of the opening and optical fibers (15) for conducting the emanating radiation are disposed in an annular array around said laser beam optical waveguide.

5. A spectral analysis device according to claim 1, characterized in that multiple openings pass through the wall of the container and are optically connected to said device and to said generating means.

6. A spectral analysis device according to claim 5, characterized in that the optical connection (15, 18) is adapted to be selectively established and to be interrupted.

7. A spectral analysis device according to claim 6, characterized in that the device is optically connected to receive emanating radiation via a movable mirror (24).

8. A spectral analysis apparatus according to claim 1, characterized in that the walls of the opening (11 and 14) are formed of metal.

9. A spectral analysis apparatus according to claim 8, characterized in that the metal walls are aluminum.

10. A spectral analysis apparatus according to claim 1, further including means for electro-optically amplifying said emanating radiation.

11. A spectral analysis apparatus according to claim 10, characterized in that said electrooptical amplification takes place in an image amplifier tube and thereafter the amplified light is converted by a photoelectric detector into an electrical signal capable of being processed by said computer.

12. A spectral analysis apparatus according to claim 1, characterized in that the exit point of the optical waveguide for the emanating radiation is formed as a rectangular aperture and is positioned in the inlet aperture of the analysis unit.

* * * * *